(12) United States Patent
Green et al.

(10) Patent No.: US 8,349,792 B2
(45) Date of Patent: Jan. 8, 2013

(54) COMBINATION COMPRISING CNDAC (2'-CYANO-2'-DEOXY-N4-PALMITOYL-1-BETA-D-ARABINOFURANOSYL-CYTOSINE) AND A CYTOTOXIC AGENT

(75) Inventors: Simon R. Green, Dundee (GB); Ian Neil Fleming, Angus (GB)

(73) Assignee: Cyclacel Limited, London (GB)

( * ) Notice: Subject to any disclaimer, the term of this patent is extended or adjusted under 35 U.S.C. 154(b) by 536 days.

(21) Appl. No.: 12/517,196

(22) PCT Filed: Dec. 19, 2007

(86) PCT No.: PCT/GB2007/004883
§ 371 (c)(1),
(2), (4) Date: Nov. 19, 2009

(87) PCT Pub. No.: WO2008/075042
PCT Pub. Date: Jun. 26, 2008

(65) Prior Publication Data
US 2010/0069291 A1    Mar. 18, 2010

(30) Foreign Application Priority Data

Dec. 19, 2006  (GB) .................................. 0625283.7

(51) Int. Cl.
| | | |
|---|---|---|
| A61K 38/00 | (2006.01) | |
| A61K 31/70 | (2006.01) | |
| A61K 31/44 | (2006.01) | |
| A61K 31/19 | (2006.01) | |
| A01N 43/04 | (2006.01) | |
| A01N 43/42 | (2006.01) | |
| A01N 37/00 | (2006.01) | |
| A01N 37/28 | (2006.01) | |

(52) U.S. Cl. ........... 514/1.1; 514/27; 514/283; 514/557; 514/575

(58) Field of Classification Search ........................ None
See application file for complete search history.

(56) References Cited

U.S. PATENT DOCUMENTS

| | | |
|---|---|---|
| 5,591,607 A | 1/1997 | Gryaznov et al. |
| 5,616,567 A | 4/1997 | Sasaki et al. |
| 5,654,420 A | 8/1997 | Matsuda et al. |
| 5,691,319 A | 11/1997 | Kaneko et al. |
| 5,824,984 A | 10/1998 | Morrow |
| 5,952,383 A | 9/1999 | Metziger et al. |
| 5,990,093 A | 11/1999 | Schinazi et al. |
| 6,245,749 B1 | 6/2001 | Schinazi et al. |
| 6,369,086 B1 | 4/2002 | Davis et al. |
| 6,462,063 B1 | 10/2002 | Ho et al. |
| 6,525,033 B1 | 2/2003 | Schinazi et al. |
| 6,787,526 B1 | 9/2004 | Bryant et al. |
| 6,812,219 B2 | 11/2004 | LaColla et al. |
| 6,822,090 B2 | 11/2004 | Morizane et al. |
| 6,908,906 B2 | 6/2005 | Takita et al. |
| 6,914,054 B2 | 7/2005 | Sommadossi et al. |
| 7,101,861 B2 | 9/2006 | Sommadossi et al. |
| 7,105,493 B2 | 9/2006 | Sommadossi et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,468,357 B2 | 12/2008 | Schinazi et al. |

(Continued)

FOREIGN PATENT DOCUMENTS

| | | |
|---|---|---|
| DE | 7304511 | 2/1974 |
| DE | 2305815 | 8/1974 |
| DE | 4419792 C1 | 2/1996 |
| EP | 0535231 B1 | 4/1993 |
| EP | 0536936 A1 | 4/1993 |
| EP | 1186612 B1 | 3/2002 |

(Continued)

OTHER PUBLICATIONS

Kumagai et al. SAHA markedly inhibits growth and induces apoptosis of human pancreatic cancer cells. Experimental and Molecular Therapeutics 4: DNA, Histone, and Proteasome Modulation. Abstract #610. Proc Amer Assoc Cancer Res, vol. 46, Apr. 2005.*

(Continued)

*Primary Examiner* — Marcela M Cordero Garcia
(74) *Attorney, Agent, or Firm* — Nelson Mullins Riley & Scarborough LLP; Cynthia L. Kanik

(57) ABSTRACT

A first aspect of the invention relates to a combination comprising 2'-cyano-2'-deoxy-$N^4$-palmitoyl-1-β-D-arabinofuranosyl-cytosine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof. A second aspect relates to a pharmaceutical product comprising (i) 2'-cyano-2'-deoxy-$N^4$-palmitoyl-1-β-D-arabinofuranosyl-cytosine, or a metabolite thereof, or a pharmaceutically acceptable salt thereof, and (ii) a cytotoxic agent selected from: (a) a HDAC inhibitor; and (b) a topoisomerase inhibitor selected from etoposide, topotecan and SN-38, or a prodrug thereof, as a combined preparation for simultaneous, sequential or separate use in therapy. A third aspect relates to a method of treating a proliferative disorder, said method comprising simultaneously, separately or sequentially administering to a subject 2'-cyano-2'-deoxy-$N^4$-palmitoyl-1-β-D-arabinofuranosyl-cytosine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof. A fourth aspect of the invention relates to the use of a subject 2'-cyano-2'-deoxy-$N^4$-palmitoyl-1-β-D-arabinofuranosyl-cytosine, or a metabolite thereof, or a pharmaceutically acceptable salt thereof, in the preparation of a medicament for treating cutaneous T-cell lymphoma (CTCL).

14 Claims, 5 Drawing Sheets

U.S. PATENT DOCUMENTS

| | | | |
|---|---|---|---|
| 7,534,772 | B2 | 5/2009 | Weiner et al. |
| 7,772,207 | B2 | 8/2010 | Green et al. |
| 7,825,103 | B2 | 11/2010 | Nomura et al. |
| 8,110,676 | B2 | 2/2012 | Bertini et al. |
| 8,124,593 | B2 * | 2/2012 | Gianella-Borradori et al. ............................ 514/49 |
| 2002/0107221 | A1 | 8/2002 | Schinazi et al. |
| 2002/0156033 | A1 | 10/2002 | Bratzler et al. |
| 2002/0161377 | A1 | 10/2002 | Rabkin |
| 2002/0165569 | A1 | 11/2002 | Ramzipoor et al. |
| 2003/0026801 | A1 | 2/2003 | Weiner et al. |
| 2003/0087873 | A1 | 5/2003 | Stuyver et al. |
| 2003/0124182 | A1 | 7/2003 | Shojaei et al. |
| 2003/0124512 | A1 | 7/2003 | Stuyver |
| 2003/0134827 | A1 | 7/2003 | Duan et al. |
| 2004/0097461 | A1 | 5/2004 | Sommadossi et al. |
| 2005/0009773 | A1 | 1/2005 | Kandimalla et al. |
| 2005/0014716 | A1 | 1/2005 | Wang et al. |
| 2005/0124532 | A1 | 6/2005 | Sommadossi et al. |
| 2005/0171096 | A1 | 8/2005 | Sheppeck et al. |
| 2006/0211369 | A1 | 9/2006 | Steelberg et al. |
| 2010/0197627 | A1 | 8/2010 | Wang et al. |
| 2011/0028421 | A1 | 2/2011 | Engel et al. |

FOREIGN PATENT DOCUMENTS

| | | |
|---|---|---|
| EP | 1364959 B1 | 11/2003 |
| EP | 1411954 B1 | 4/2004 |
| EP | 1669364 A2 | 6/2006 |
| EP | 1736478 A1 | 12/2006 |
| WO | 97/11647 A1 | 4/1997 |
| WO | 00/67760 A1 | 11/2000 |
| WO | 01/79248 A1 | 10/2001 |
| WO | 01/92282 A2 | 12/2001 |
| WO | 01/97843 A2 | 12/2001 |
| WO | 02/28829 A2 | 4/2002 |
| WO | 02/32920 A2 | 4/2002 |
| WO | 02/46182 A1 | 6/2002 |
| WO | 02/064609 A1 | 8/2002 |
| WO | 03/039536 A1 | 5/2003 |
| WO | 2004/091441 A2 | 10/2004 |
| WO | 2004/103301 A2 | 12/2004 |
| WO | 2005/000204 A2 | 1/2005 |
| WO | 2005/053699 A1 | 6/2005 |
| WO | 2005/115410 A2 | 12/2005 |
| WO | 2005/123061 A1 | 12/2005 |
| WO | 2006/013203 A2 | 2/2006 |
| WO | 2006/080509 A1 | 8/2006 |
| WO | 2007/054731 A1 | 5/2007 |
| WO | 2007/072061 A2 | 6/2007 |
| WO | 2008/010571 A1 | 1/2008 |
| WO | 2008/075042 A1 | 6/2008 |
| WO | 2009/067409 A1 | 5/2009 |
| WO | 2009/129120 A2 | 10/2009 |
| WO | 2009/133963 A1 | 11/2009 |
| WO | 2009/136162 A1 | 11/2009 |
| WO | 2010/131475 A1 | 11/2010 |
| WO | 2011/004540 A1 | 1/2011 |
| WO | 2011/067588 A1 | 6/2011 |
| WO | 2011/104540 A1 | 9/2011 |

OTHER PUBLICATIONS

Accession No. 2000-565332, Hanaoka, K. et al., "Antitumor liposome preparations comprise sterol compound, phosphatidylcholine compound and 1-(2'-cyano-2'-deoxy-beta-arabino-pentofuranosyl) cytosine," (2000).

Accession No. 2001-040935, Hanaoka, K. et al., "Liposome preparation with high drug transfer contains 1-(2-C-cyano-2-deoxy-beta-D-arabinopentofuranosyl)-N4-palmitoyl cytosine antitumor agent," (2001).

Bible, Keith C. et al., "Cytotoxic Synerty between Flavopiridol (NSC 649890, L86-8275) and Various Antineoplastic Agents: The Importance of Sequence of Administration," Cancer Research, vol. 57:3375-3380 (1997).

Burch, P.A. et al., "Phase I Study of Orally Administered CS-682 in Solid Tumors," Proceedings of ASCO, vol. 20:92a, Poster No. 364 (2001).

CAplus, Accession No. 136:310184, Chong, Lee et al., "Preparation of hydroxamic acid peptide deformylase inhibitors as antibacterial agents," (2011).

Danesi, Romano et al., "Pharmacogenetic determinants of anti-cancer drug activity and toxicity," Trends in Pharmacological Science, vol. 22*8):420-426 (2001).

Delaunoit, Thierry et al., "A phase I clinical and pharmacokinetic study of CS-682 administered orally in advanced malignant solid tumors," Investigational New Drugs, vol. 24:327-333 (2006).

Donehower, Ross et al., "A Phase I Study of CS-682, an Oral Antimetabolite, in Patients with Refractory Solid Tumors," 2000 ASCO Meeting, Proc. Am. Soc. Clin. Oncol., vol. 19, Abstract No. 764 (2000).

Fujita, F. et al., "Antitumor activity of a novel nucleoside 1-(2-C-cyano-2-deoxy-beta-D-arabino-pentofuranosy)-N4-palmitoylcytosine (CS-682)," Proceedings of the American Association for Cancer Research, 88th Annual Meeting, vol. 38:101-102, Abstract No. 681 (1997).

Gilbert, Jill et al., "A Phase I study of the oral antimetabolite, CS-682, administered once daily 5 days per week in patients with refractory solid tumor malignancies," Invest. New Drugs, vol. 24:499-508 (2006).

Hanaoka, K. et al., "A novel mechanism of action of a new antitumor nucleoside 1-(2-C-cyano-2-deoxy-beta-D-arabino-pentofuranosyl)-N4-Palmitoylcytosine (CS-682)," Proceedings of the American Association for Cancer Research, 88th Annual Meeting, vol. 38:101, Abstract No. 680 (1997).

Hanaoka, Kenji et al., "Antitumor Activity and Novel DNA-Self-Strand-Breaking Mechanism of CNDAC (1-(2-C-cyano-2-deoxy-b-D-arabino-pentofuranosyl) cytosine) and its N4-Palmitoyl Derivative (CS-682)," Int. J. Cancer, vol. 82:226-236 (1999).

Kaneko, M. et al., "Synthesis and antitumor activity of a novel antitumor nucleoside 1-(2-C-cyano-2-deoxy-beta-D-arabino-pentofuranosyl)-N4-palmitoylcytosine (CS-682)," Proceedings of the American Association for Cancer Research, 88th Annual Meeting, vol. 38:101, Abstract No. 679 (1997).

Liu, Xiaojun et al., "Molecular Basis for G2 Arrest Induced by 2-C-Cyano-2-Deoxy-1-Beta-D-Arabino-Pentofuranosylcytosine and Consequences of Checkpoint Abrobation," Cancer Res., vol. 65(15):6874-6881 (2005).

Peckham, Michael et al., "Biological and Pharmacological Basis of Chemotherapy, Biological Basis," Oxford Textbook of Oncology, vol. 1, Oxford University Press, Oxford, England, pp. 447-453 (1995).

Sankyo Co., Ltd., "CS-682," Drugs of the Future, vol. 24(9):957-960 (1999).

Serova, M. et al., "Antiproliferative effects of sapacitabine (CYC682), a novel 2'-deoxycytidine-derivative, in human cancer cells," British Journal of Cancer, vol. 97:628-636 (2007).

Silverman, Richard B., "Drug Discovery, Design, and Development," The Organic Chemistry of Drug Design and Drug Action, Academic Press, San Diego, Chapter 2, pp. 4-47 (1992).

STN Gen Caesar Accession No. 1364, "Cyclacel's cancer drug starts Phase II testing," (2002).

STN Database Descriptions, "Rapra," 2006 Chemical Abstracts Catalog, Chemical Abstracts Service, p. 52 (2006).

The Merck Manual of Diagnosis and Therapy, Seventeenth Edition, Mark H. Beers (Ed.), Merck Research Laboratories, Whitehouse Station, N.J., pp. 397-398, 948-949, 1916 and 1979-1981 (1999).

Tolcher, A. et al., "Phase I study of sapacitabine, an oral nucleoside analogue, in patients with refractory solid tumors or lymphomas," European Journal of Cancer, Supplement, vol. 4(12):142, Poster No. 463 (2006).

Vippagunta, Sudha R. et al., "Crystalline solids," Advanced Drug Delivery Reviews, vol. 48:3-26 (2001).

Whittaker, Mark et al., "Design and Therapeutic Application of Matrix Metalloproteinase Inhibitors," Chem. Rev., vol. 99:2735-2776 (1999).

Whittaker, Mark et al., "MMP-12 inhibitors, AstraZeneca: WO2004020415," Expert Opin. Ther. Patents, vol. 14 (11):1637-1640 (2004).

Wu, Ming et al., "High-Resolution Magnetic Resonance Imaging of the Efficacy of the Cytosine Analogue 1-[2-C-Cyano-2-deoxy-b-D-arabino-pentofuranosyl]-N4-palmitoyl Cytosine (CS-682) in a Liver-Metastasis Athymic Nude Mouse Mode," Cancer Research, vol. 63:2477-2482 (2003).

International Preliminary Report on Patentability for Application No. PCT/GB2006/004230, dated May 14, 2008.

International Search Report for Application No. PCT/GB2006/004230, dated Feb. 5, 2007.

International Search Report for Application No. PCT/GB2006/004927, dated Aug. 6, 2007.

Written Opinion for Application No. PCT/GB2004/005081, dated Jun. 7, 2006.

Written Opinion for Application No. PCT/GB2006/004927, dated Aug. 6, 2007.

\* cited by examiner

COMBINATION COMPRISING CNDAC (2'-CYANO-2'-DEOXY-N4-PALMITOYL-1-BETA-D-ARABINOFURANOSYL-CYTOSINE) AND A CYTOTOXIC AGENT

RELATED APPLICATIONS

The present application is a 35 U.S.C. 371 national stage filing of International Application No. PCT/GB2007/004883, filed Dec. 19, 2007, which claims priority to Great Britain Application No. 0625283.7, filed Dec. 19, 2006. The entire contents of each of these applications are hereby incorporated by reference herein.

The present invention relates to a combination suitable for the treatment of proliferative disorders.

BACKGROUND TO THE INVENTION

The therapeutic use of pyrimidine nucleosides in the treatment of proliferative disorders has been well documented in the art. By way of example, commercially available antitumor agents of the pyrimidine series include 5-fluorouracil (Duschinsky, R., et al., J. Am. Chem. Soc., 79, 4559 (1957)), Tegafur (Hiller, S A., et al., Dokl. Akad. Nauk USSR, 176, 332 (1967)), UFT (Fujii, S., et al., Gann, 69, 763 (1978)), Carmofur (Hoshi, A., et al., Gann, 67, 725 (1976)), Doxyfluridine (Cook, A. F., et al., J. Med. Chem., 22, 1330 (1979)), Cytarabine (Evance, J. S., et al., Proc. Soc. Exp. Bio. Med., 106. 350 (1961)), Ancytabine (Hoshi, A., et al., Gann, 63, 353, (1972)) and Enocytabine (Aoshima, M., et al., Cancer Res., 36, 2726 (1976)).

Nucleoside analogues that show antimetabolic activity in cancer cells have been successfully used in the treatment of various human malignancies. Nucleosides such as 1-beta-D-arabinofuranosylcytosine (Ara-C), fludarabine and cladribine play an important role in the treatment of leukemias, while gemcitabine is extensively used in the treatment of many types of solid tumors. These compounds are metabolized in a similar manner to endogenous nucleosides and nucleotides. Active metabolites interfere with the de novo synthesis of nucleosides and nucleotides and/or inhibit DNA chain elongation after being incorporated into DNA strands, acting as chain terminators. Furthermore, nucleoside antimetabolites incorporated into DNA strands induce strand-breaks that may eventually result in induction of apoptosis.

Nucleoside antimetabolites target one or more specific enzyme(s) (Galmarini et al, Nucleoside analogues and nucleobases in cancer treatment. Lancet Oncol. 2002 July; 3(7):415-24; Review). The mode of inhibitory action on target enzymes may differ between nucleoside antimetabolites, which have the same nucleoside base, such as Ara-C and gemcitabine. Although both nucleosides are phosphorylated by deoxycytidine kinase and are also good substrates of cytidine deaminase, only gemcitabine shows antitumor activity against solid tumors. This suggests that there are differences in the pharmacological activity of these nucleoside antimetabolites, which may reflect different modes of action on target molecules.

It has been shown that dCK deficiency is associated with resistance to Ara-C in various cell and animal models (Galmarini et al, In vivo mechanisms of resistance to cytarabine in acute myeloid leukaemia, Br J Haematol. 2002 June; 117(4): 860-8). Alterations in expression of the dCK gene or significant decrease in the activity of this enzyme in Ara-C-treated AML patients have also been correlated with clinical outcome. These data are consistent with the concept that intracellular phosphorylation of Ara-C by dCK is essential for cytotoxicity in cellular models and in patients. Deficiency of hENT1 in blast cell plasma membranes has also been suggested as a mechanism of cellular resistance to Ara-C. Other authors have suggested that mechanisms of drug resistance to Ara-C are associated with increased levels of Ara-C catabolic enzymes such as CDA.

EP 536936 (Sankyo Company Limited) discloses various 2'-cyano-2'-deoxy-derivatives of 1-β-D-arabinofuranosylcytosine which have been shown to exhibit valuable anti-tumour activity. One particular compound disclosed in EP 536936 is 2'-cyano-2'-deoxy-N$^4$-palmitoyl-1-β-D-arabinofuranosylcytosine (referred to hereinafter as "sapacitabine"), this compound is currently under further investigation.

Sapacitabine, also known as CYC682 and 1-(2-C-cyano-2-dioxy-β-D-arabino-pentofuranosyl)-N$^4$-palmitoyl cytosine (Hanaoka, K., et al, Int. J. Cancer, 1999:82:226-236; Donehower R, et al, Proc Am Soc Clin Oncol, 2000: abstract 764; Burch, P A, et al, Proc Am Soc Clin Oncol, 2001: abstract 364), is an orally administered novel 2'-deoxycytidine antimetabolite prodrug of the nucleoside CNDAC, 1-(2-C-cyano-2-deoxy-β-D-arabino-pentafuranosyl)-cytosine.

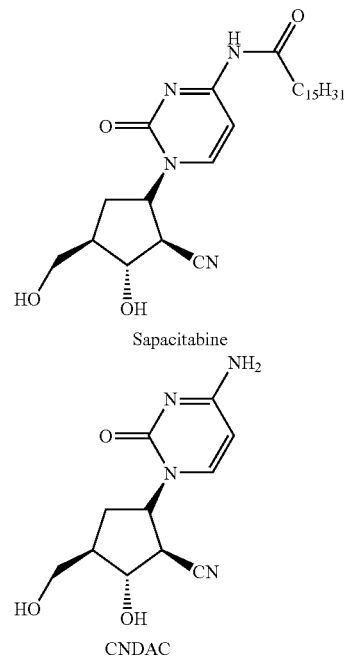

Sapacitabine has a unique mode of action over other nucleoside metabolites such as gemcitabine in that it has a spontaneous DNA strand breaking action, resulting in potent anti-tumour activity in a variety of cell lines, xenograft and metastatic cancer model (Hanaoka et al, 1999; Kaneko et al, 1997; Wu et al, 2003). Because of its unique mode of action, sapacitabine causes a block at the G2/M phase of the cell cycle rather than in S phase of the cell cycle, which is seen for gemcitabine and ara-C (Azuma et al 2001).

Sapacitabine has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that sapacitabine exhibited strong anticancer activity in a model of colon cancer. In the same model, sapacitabine was found to be superior to either gemcitabine or 5-FU in terms of increasing survival and also preventing the spread of colon cancer metastases to the liver (Wu M, et al, *Cancer Research,* 2003: 63:2477-2482). To date, phase I data from patients with a variety of cancers suggest that sapacitabine is well tolerated in humans, with myelosuppression as the dose limiting toxicity.

It well established in the art that active pharmaceutical agents can often be administered in combination in order to optimise the treatment regime. For example, combinations comprising a CDK inhibitor and 1-(2-C-cyano-2-dioxy-β-D-arabino-pentofuranosyl)-N4-palmitoyl cytosine, or a metabolite thereof, and their use in the treatment of proliferative disorders are disclosed in WO 2005/053699 (Cyclacel Limited).

The present invention seeks to provide new combinations of known pharmaceutical agents that are particularly suitable for the treatment of proliferative disorders, especially cancer. More specifically, the invention relates to combinations comprising 2'-cyano-2'-deoxy-$N^4$-palmitoyl-1-β-D-arabinofuranosyl-cytosine, or a metabolite thereof, or a pharmaceutically acceptable salt thereof, with various cytotoxic drugs.

Although 2'-cyano-2'-deoxy-$N^4$-palmitoyl-1-β-D-arabinofuranosyl-cytosine and these cytotoxic drugs are well established in the art as individual therapeutic agents, to date there has been no suggestion that the specific combinations claimed herein would be effective in the treatment of cancer.

STATEMENT OF THE INVENTION

A first aspect of the invention relates to a combination comprising 2'-cyano-2'-deoxy-$N^4$-palmitoyl-1-β-D-arabinofuranosyl-cytosine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof.

A second aspect relates to a pharmaceutical composition comprising a combination according to the invention and a pharmaceutically acceptable carrier, diluent or excipient.

A third aspect relates to a pharmaceutical product comprising (i) 2'-cyano-2'-deoxy-$N^4$-palmitoyl-1-β-D-arabinofuranosyl-cytosine, or a metabolite thereof, or a pharmaceutically acceptable salt thereof, and (ii) a cytotoxic agent selected from: (a) a HDAC inhibitor; and (b) a topoisomerase inhibitor selected from etoposide, topotecan and SN-38, or a prodrug thereof, as a combined preparation for simultaneous, sequential or separate use in therapy.

A fourth aspect relates to a method of treating a proliferative disorder, said method comprising simultaneously, separately or sequentially administering to a subject 2'-cyano-2'-deoxy-$N^4$-palmitoyl-1-β-D-arabinofuranosyl-cytosine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof.

A fifth aspect relates to the use of a combination according to the invention in the preparation of a medicament for treating a proliferative disorder.

A sixth aspect relates to the use of 2'-cyano-2'-deoxy-$N^4$-palmitoyl-1-β-D-arabinofuranosyl-cytosine, or a metabolite thereof, or a pharmaceutically acceptable salt thereof, in the preparation of a medicament for the treatment of a proliferative disorder, wherein said treatment comprises simultaneously, separately or sequentially administering to a subject a cytotoxic agent selected from: (a) a HDAC inhibitor; and (b) a topoisomerase inhibitor selected from etoposide, topotecan and SN-38, or a prodrug thereof.

A seventh aspect relates to the use of a cytotoxic agent selected from: (a) a HDAC inhibitor; and (b) a topoisomerase inhibitor selected from etoposide, topotecan and SN-38, or a prodrug thereof, in the preparation of a medicament for the treatment of a proliferative disorder, wherein said treatment comprises simultaneously, separately or sequentially administering to a subject 2'-cyano-2'-deoxy-$N^4$-palmitoyl-1-β-D-arabinofuranosyl-cytosine, or a metabolite thereof, or a pharmaceutically acceptable salt thereof.

An eighth aspect relates to a kit of parts comprising:
  (i) 2'-cyano-2'-deoxy-$N^4$-palmitoyl-1-β-D-arabinofuranosyl-cytosine, or a metabolite thereof, or a pharmaceutically acceptable salt thereof, optionally admixed with a pharmaceutically acceptable diluent, excipient or carrier; and
  (ii) a cytotoxic agent selected from: (a) a HDAC inhibitor; and (b) a topoisomerase inhibitor selected from etoposide, topotecan and SN-38, or a prodrug thereof, optionally admixed with a pharmaceutically acceptable diluent, excipient or carrier.

A ninth aspect of the invention relates to the use of 2'-cyano-2'-deoxy-$N^4$-palmitoyl-1-β-D-arabinofuranosyl-cytosine, or a metabolite thereof, or a pharmaceutically acceptable salt thereof, in the preparation of a medicament for treating cutaneous T-cell lymphoma (CTCL).

A tenth aspect of the invention relates to a method of treating cutaneous T-cell lymphoma (CTCL) in a subject, said method comprising administering to said subject a therapeutically effective amount of 2'-cyano-2'-deoxy-$N^4$-palmitoyl-1-β-D-arabinofuranosyl-cytosine, or a metabolite thereof, or a pharmaceutically acceptable salt thereof.

DETAILED DESCRIPTION

The preferred embodiments set out below are applicable to all the above-mentioned aspects of the invention.

The present invention relates to the use of 2'-cyano-2'-deoxy-$N^4$-palmitoyl-1-β-D-arabinofuranosyl-cytosine, or a metabolite thereof, (i) in combination with various other therapeutic agents in the treatment of cutaneous T-cell lymphoma (CTCL), or (ii) in monotherapy in the treatment of cutaneous T-cell lymphoma (CTCL).

In one preferred embodiment, the metabolite of 2'-cyano-2'-deoxy-$N^4$-palmitoyl-1-β-D-arabinofuranosyl-cytosine is 1-(2-C-cyano-2-deoxy-β-D-arabino-pentafuranosyl)-cytosine (otherwise known as CNDAC).

As mentioned above, one aspect of the present invention relates to a combination comprising 2'-cyano-2'-deoxy-$N^4$-palmitoyl-1-β-D-arabinofuranosyl-cytosine, or a metabolite thereof, or a pharmaceutically acceptable salt thereof, and a selected cytotoxic agent which is a HDAC inhibitor.

Histones are small positively charged proteins that are rich in basic amino acids (positively charged at physiological pH). There are five main types of histones namely, H1, H2A, H2B, H3, and H4, which exhibit a high degree of structural similarity.

Histones are not found in eubacteria (e.g., *E. coli*), although the DNA of these bacteria is associated with other proteins that presumably function like histones to package the DNA within the bacterial cell. Archaebacteria, however, do contain histones that package their DNAs in structures similar to eukaryotic chromatin (G. M. Cooper, "The Cell—A Molecular Approach", $2^{nd}$ Edition, Chapter II).

The majority of histones are synthesized during the S phase of the cell cycle, and newly synthesized histones quickly enter the nucleus to become associated with DNA. Within minutes of its synthesis, new DNA becomes associated with histones in nucleosomal structures.

The amino-terminal tail domains of histones may be enzymatically modified by post-translational addition of methyl (to lysine and arginine groups), acetyl (to lysine groups), or phosphate groups (to serine groups) (Spencer et al, Gene, 1999, 240(1), 1). This results in a reduction of the net positive charge of the histone which, consequently, may weaken the binding of the histone to DNA.

Studies of histone deacetylators (HDACs), as well as the compounds which inhibit HDACs, have elucidated the mechanisms through which some disease states act. For example, in the search for novel anti-malarial compounds, the naturally occurring apicidin was shown to inhibit the in vitro growth of P. falciparum by hyperacetylating histones (K. T. Andrews et al, Int. J. Parasitol., 2000, 30(6), 761).

HDACs are therefore believed to be associated with a number of different diseases which include proliferative disorders such as leukemia (Lin et al, Nature, 1998, 391, 811), melanomas/squamous cell carcinomas (Gillenwater et al, Int. J. Cancer, 1998, 75217; Saunders et al, Cancer Res., 1999, 59, 399), breast cancer, prostrate cancer, bladder cancer (Gelmetti et al, Mol. Cell. Biol., 1998, 18, 7185; Wang et al, PNAS, 1998, 951, 10860) and colon cancer (C. A. Hassig, et al, 1997, Chem. Biol., 4, 783; S. Y. Archer et al, PNAS, 1998, 95(12), 6791).

To date, there has been no disclosure of the specific combinations claimed in the present application, let alone any suggestion that they would be therapeutically useful in the treatment of cancers such as cutaneous T-cell lymphoma (CTCL) and non-small cell lung cancer (NSCLC).

In one preferred embodiment, the HDAC inhibitor is selected from sodium butyrate, or a prodrug thereof, suberoylanilide hydramic acid (SAHA), sodium valproate, valproic acid, trichostatin A (TSA), PXD101, LAQ824, MS-275, CI-994, SB939, MGCD0103, and depsipeptide.

In a particularly preferred embodiment of the invention, the HDAC inhibitor is sodium butyrate, or a prodrug thereof.

In a highly preferred embodiment, the prodrug of sodium butyrate is pivaloyloxymethyl butyrate.

In another particularly preferred embodiment, the HDAC inhibitor is suberoylanilide hydramic acid (SAHA).

In yet another particularly preferred embodiment, the HDAC inhibitor is sodium valproate or valproic acid.

In another particularly preferred embodiment, the HDAC inhibitor is trichostatin A (TSA).

In one highly preferred embodiment, the combination comprises sapacitabine and SAHA.

In another highly preferred embodiment, the combination comprises CNDAC and SAHA.

In one highly preferred embodiment, the combination comprises sapacitabine and sodium valproate or valproic acid.

In another highly preferred embodiment, the combination comprises CNDAC and sodium valproate or valproic acid.

As mentioned above, another aspect of the present invention relates to a combination comprising 2'-cyano-2'-deoxy-$N^4$-palmitoyl-1-β-D-arabinofuranosyl-cytosine, or a metabolite thereof, or a pharmaceutically acceptable salt thereof, and a cytotoxic agent which is a topoisomerase inhibitor selected from etoposide, topotecan and SN-38, or a prodrug thereof.

DNA molecules can coil and bend in space, leading to changes in topology, including formation of negative or positive supercoils. The enzymes that control the topology of DNA function at several different steps in replication in both prokaryotic and eukaryotic cells. There are two classes of topoisomerases namely, topoisomerase I and topoisomerase II. Thus, in one preferred embodiment, the topoisomerase inhibitor is a topoisomerase I inhibitor, whereas in another preferred embodiment, the topoisomerase inhibitor is a topoisomerase II inhibitor.

Type I topoisomerases relax DNA by nicking and then closing one strand of duplex DNA. Type II topoisomerases change DNA topology by breaking and rejoining double-stranded DNA (Molecular Cell Biology, 4$^{th}$ Edition, Eds. H. Lodish et al, 2000, WH Freeman & Company). Topoisomerase inhibitors are believed to bind to DNA, the topoisomerase, or either molecule at or near the region of the enzyme involved in the formation of the DNA-protein covalent linkage (Holland & Frei Cancer Medicine 6, Eds. Kufe et al, 2003, BC Decker Inc.)

In one highly preferred embodiment, the topoisomerase inhibitor is SN-38, or a prodrug thereof.

SN-38 [(+)-(4S)-4,11-diethyl-4,9-dihydroxy-1H-pyrano[3',4':6,7]-indolizino[1,2-]quinoline-3,14(4H,12H)-dione], also known as 7-ethyl-10-hydroxy-20(S)-camptothecin, has the structure shown below.

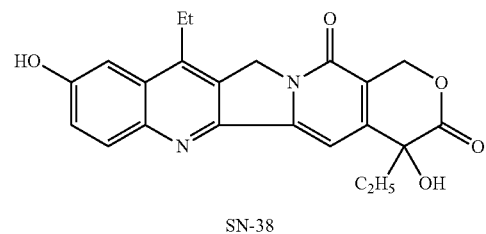 [SMILES: CCc1c2c(nc3ccc(O)cc13)-c1cc3c(c(=O)n1C2)COC(=O)C3(O)CC ; "SN-38"]

SN-38

SN-38 is the active metabolite of irinotecan (also known as CPT-11) which is a hemisynthetic, water-soluble derivative of camptothecin used for the treatment of cancer, i.e. CPT-11 is a prodrug of SN-38 that is metabolized to its active form, SN-38. In a highly preferred embodiment, the combination of the invention comprises a prodrug of SN-38. Preferably, the prodrug is irinotecan.

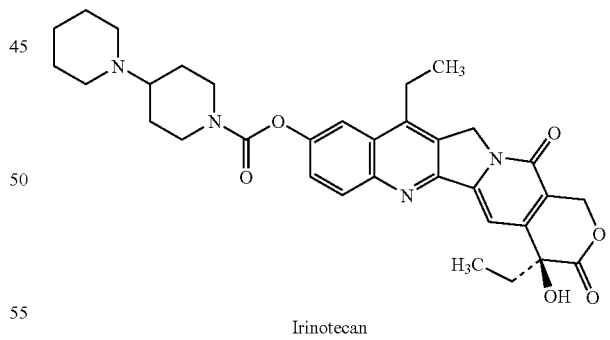

Irinotecan

Irinotecan is a DNA topoisomerase I inhibitor that induces double strand breaks. Irinotecan is converted in vivo into its active form SN-38, with cytotoxic effects exerted through its binding to and inhibition of the DNA-associated nuclear enzyme topoisomerase I (top 1), thus stabilizing top 1 DNA cleavable ternary complexes (Tanizawa, A. et al, J. Natl. Cancer Inst., 86: 836-42, 1994). This impedes the DNA-religation reaction and results in DNA double-strand breaks, eventually leading to apoptosis (Kjeldsen, E. et. al, J. Mol. Biol., 228: 1025-30, 1992).

Irinotecan is approved for use in the treatment of patients with advanced colorectal cancer (i) in combination with 5-fluorouracil and folinic acid in patients without prior chemotherapy for advanced disease; and (ii) as a single agent in patients who have failed to respond to an established 5-fluorouracil containing treatment regimen.

In another preferred embodiment, the topoisomerase inhibitor is etoposide.

Etoposide [4'-demethylepipodophyllotoxin 9-[4,6-O—(R)-ethylidene-β-D-gluco-pyranoside] is a semisynthetic derivative of podophyllotoxin, a toxin found in the American May apple. Etoposide has the chemical structure shown below:

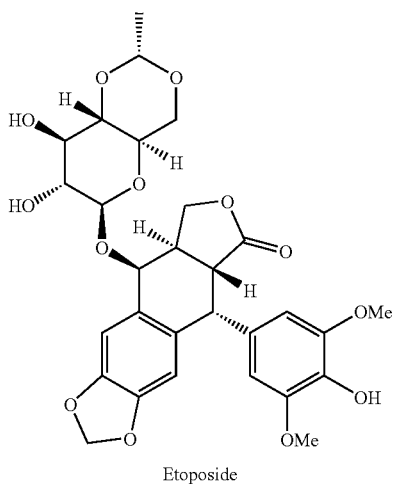 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O]

Etoposide

Etoposide is approved for use in combination with other approved chemotherapeutic agents (i) in patients with refractory testicular tumours who have already received appropriate surgical, chemotherapeutic and radiotherapeutic therapy; and (ii) in patients as the first line treatment of small cell lung cancer (source: www.rxlist.com).

In another preferred embodiment, the topoisomerase inhibitor is topotecan.

Topotecan hydrochloride is a semi-synthetic derivative of camptothecin and is an anti-tumor drug with topoisomerase I-inhibitory activity. Topotecan has the structure shown below and the chemical name (S)-10-[(dimethylamino)methyl]-4-ethyl-4,9-dihydroxy-1H-pyrano[3',4':6,7]indolizino[1,2-b]quinoline-3,14-(4H,12H)-dione monohydrochloride.

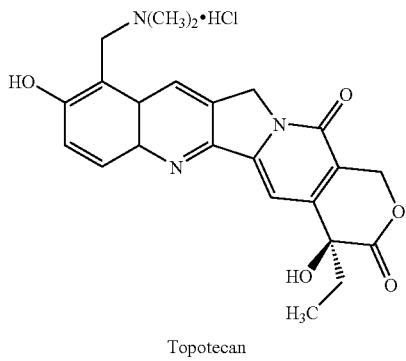

Topotecan

It has the molecular formula $C_{23}H_{23}N_3O_5 \cdot HCl$ and a molecular weight of 457.9. It is soluble in water and melts with decomposition at 213° to 218° C.

Topoisomerase I relieves torsional strain in DNA by inducing reversible single strand breaks. Topotecan binds to the topoisomerase I-DNA complex and prevents religation of these single strand breaks. The cytotoxicity of topotecan is thought to be due to double strand DNA damage produced during DNA synthesis, when replication enzymes interact with the ternary complex formed by topotecan, topoisomerase I, and DNA. Mammalian cells cannot efficiently repair these double strand breaks.

To date, there has been no suggestion of administering a combination comprising sapacitabine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof.

Many anti-cancer agents are given in combination in order to optimise the treatment regime. The effect of drug combinations is inherently unpredictable and there is often a propensity for one drug to partially or completely inhibit the effects of the other.

The present invention is based on the surprising observation that administering a combination comprising sapacitabine, or a metabolite, or a pharmaceutically acceptable salt thereof, and a cytotoxic agent, either simultaneously, separately or sequentially, does not lead to any significant or dramatic adverse interaction between the two agents.

The unexpected absence of any such antagonistic interaction is critical for clinical applications.

Preferably, the combination of the invention is a synergistic combination comprising a sapacitabine, or a metabolite, or a pharmaceutically acceptable salt thereof and the cytotoxic agent, i.e. the combination has a synergistic effect.

In a preferred embodiment, the combination of sapacitabine, or metabolite thereof, or pharmaceutically acceptable salt thereof, and the cytotoxic agent produces an enhanced effect as compared to either drug administered alone. The surprising nature of this observation is in contrast to that expected on the basis of the prior art. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

In another preferred embodiment, sapacitabine, or metabolite thereof, or a pharmaceutically acceptable salt thereof, and the cytotoxic agent interact in a manner so as to alleviate or eliminate adverse side effects associated with the use of the individual components in monotherapy, or associated with their use in known combinations.

As mentioned above, one aspect of the invention relates to a pharmaceutical product comprising (i) 2'-cyano-2'-deoxy-N$^4$-palmitoyl-1-β-D-arabinofuranosyl-cytosine, or a metabolite thereof, or a pharmaceutically acceptable salt thereof, and (ii) a cytotoxic agent selected from: (a) a HDAC inhibitor; and (b) a topoisomerase inhibitor selected from etoposide, topotecan and SN-38, or a prodrug thereof, as a combined preparation for simultaneous, sequential or separate use in therapy.

The combination comprising 2'-cyano-2'-deoxy-N$^4$-palmitoyl-1-β-D-arabinofuranosyl-cytosine, or a metabolite thereof, or a pharmaceutically acceptable salt thereof, and the cytotoxic agent may be administered simultaneously, sequentially or separately (as part of a dosing regime).

As used herein, "simultaneously" is used to mean that the two agents are administered concurrently. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "sequentially", "separately" is used herein to mean that the gap between administering one agent and the other is significant i.e. the first administered agent may no longer be present in the bloodstream in a therapeutically effective amount when the second agent is administered.

In one preferred embodiment, the second agent is administered at least 2 hours, more preferably at least 4 hours, even more preferably at least 8 hours, even more preferably still at least 12 or 24 or 48 hours after the first agent. In one particularly preferred embodiment, the second agent is administered at least 24 hours after the first agent.

One aspect the present invention relates to the use of 2'-cyano-2'-deoxy-$N^4$-palmitoyl-1-β-D-arabinofuranosyl-cytosine, or a metabolite thereof, or a pharmaceutically acceptable salt thereof, in the preparation of a medicament for the treatment of a proliferative disorder, wherein said treatment comprises simultaneously, sequentially or separately administering to a subject a cytotoxic agent selected from (a) a HDAC inhibitor; and (b) a topoisomerase inhibitor selected from etoposide, topotecan and SN-38, or a prodrug thereof.

Preferably, sapacitabine, or a metabolite thereof, or a pharmaceutically acceptable salt thereof, and the cytotoxic agent are administered sequentially or separately.

Preferably, sapacitabine, or a metabolite thereof, or a pharmaceutically acceptable salt thereof, is administered at least 2 hours, more preferably at least 4 hours, even more preferably at least 8 hours, even more preferably still at least 12 or 24 or 48 hours before the cytotoxic agent. In one particularly preferred embodiment, sapacitabine, or a metabolite thereof, or a pharmaceutically acceptable salt thereof, is administered at least 24 hours before the cytotoxic agent.

In one preferred embodiment, sapacitabine, or a metabolite thereof, or a pharmaceutically acceptable salt thereof, and the cytotoxic agent are administered simultaneously.

In another aspect, the present invention relates to the use of a cytotoxic agent selected from: (a) a HDAC inhibitor; and (b) a topoisomerase inhibitor selected from etoposide, topotecan and SN-38, or a prodrug thereof, in the preparation of a medicament for the treatment of a proliferative disorder, wherein said treatment comprises simultaneously, separately or sequentially administering to a subject 2'-cyano-2'-deoxy-$N^4$-palmitoyl-1-β-D-arabinofuranosyl-cytosine, or a metabolite thereof, or a pharmaceutically acceptable salt thereof.

In one preferred embodiment, the cytotoxic agent and sapacitabine, or a metabolite thereof, or a pharmaceutically acceptable salt thereof, are administered simultaneously or sequentially.

In one highly preferred embodiment, the cytotoxic agent is administered at least 2 hours, more preferably at least 4 hours, even more preferably at least 8 hours, even more preferably still at least 12 or 24 or 48 hours before sapacitabine, or a metabolite thereof, or a pharmaceutically acceptable salt thereof. In one particularly preferred embodiment, the cytotoxic agent is administered at least 24 hours before sapacitabine, or a metabolite thereof, or a pharmaceutically acceptable salt thereof.

In another preferred embodiment, the cytotoxic agent and 2'-cyano-2'-deoxy-$N^4$-palmitoyl-1-β-D-arabinofuranosyl-cytosine, or a metabolite thereof, or a pharmaceutically acceptable salt thereof, are administered simultaneously.

Another aspect of the invention relates to a method of treating a proliferative disorder, said method comprising simultaneously, separately or sequentially administering to a subject 2'-cyano-2'-deoxy-$N^4$-palmitoyl-1-β-D-arabinofuranosyl-cytosine, or a metabolite thereof, or a pharmaceutically acceptable salt thereof, and a cytotoxic agent selected from: (a) a HDAC inhibitor; and (b) a topoisomerase inhibitor selected from etoposide, topotecan and SN-38, or a prodrug thereof.

Preferably, the subject is a mammal, more preferably a human.

In one preferred embodiment, sapacitabine, or a metabolite thereof, or a pharmaceutically acceptable salt thereof, and the cytotoxic agent are each administered in a therapeutically effective amount with respect to the individual components.

In an alternative preferred embodiment, sapacitabine, or a metabolite thereof, or a pharmaceutically acceptable salt thereof, and the cytotoxic agent are each administered in a sub-therapeutically effective amount with respect to the individual components.

The term "sub-therapeutically effective amount" means an amount that is lower than that typically required to produce a therapeutic effect with respect to treatment with sapacitabine, or a metabolite thereof, or a pharmaceutically acceptable salt thereof, or the cytotoxic agent alone.

In a particularly preferred embodiment, sapacitabine, or a metabolite thereof, or a pharmaceutically acceptable salt thereof, and the cytotoxic agent are administered simultaneously.

In another particularly preferred embodiment, sapacitabine, or a metabolite thereof, or a pharmaceutically acceptable salt thereof, are administered sequentially or separately.

In a highly preferred embodiment, sapacitabine, or a metabolite thereof, or a pharmaceutically acceptable salt thereof, is administered sequentially or separately prior to the cytotoxic agent.

In another highly preferred embodiment, the cytotoxic agent is administered sequentially or separately prior to sapacitabine, or a metabolite thereof, or a pharmaceutically acceptable salt thereof.

Another aspect relates to the use of a combination of the present invention in the preparation of a medicament for treating a proliferative disorder.

As used herein, the phrase "preparation of a medicament" includes the use of one or more of the above described components directly as the medicament or in any stage of the manufacture of such a medicament.

Proliferative Disorder

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required.

In respect of all of the above aspects and embodiments, preferably the proliferative disorder is cancer.

In one particularly preferred embodiment, the cancer is lymphoma, preferably non-Hodgkin's lymphoma, more preferably cutaneous T-cell lymphoma (CTCL).

Cutaneous T cell lymphoma (CTCL; also known as Mycosis fungoides, Sezary syndrome or reticulum cell sarcoma of the skin) is a particular rare type of lymphoma in which cancerous T cells grow within the skin.

CTLC is a rare condition with no known cause. There are only about 4 cases diagnosed for every million people and most patients are between 40 and 60 years old. The condition is twice as common in men and slightly more common in black people. It can only be definitely diagnosed by taking a biopsy and examining under a microscope for cancerous T cells.

There are four main stages of the condition. Stage 1 affects only the skin; in stage 2, the lymph nodes are enlarged, but there is no sign of cancer inside them; in stage 3, there are lymphoma cells in the lymph nodes; and in stage 4, the lymphoma has spread to body organs.

The prognosis of CTCL depends on how widespread the disease is. If less than 10% of the skin is affected, there is a good chance of complete cure or long term control. If more than 10% of the skin is involved, or if the lymphoma has spread to the lymph nodes or a body organ, then the disease is usually incurable, but can still be controlled with long term treatment.

Treatment of CTCL depends on the stage of the disease at diagnosis. Conventional treatments to date include topical chemotherapy, treatment with ultraviolet light (PUVA; psoralen ultraviolet treatment), radiotherapy, electron beam therapy (EBT) and oral or injected chemotherapy. Chemotherapy is generally only used when CTLC is advanced. CTLC responds well to chemotherapy, but the effects are short lived. Other treatments under investigation include interferon, Denileukin (Ontak), Campath 1H (Alemtuzumub), Bexarotene and Depsipeptide (FK228).

In another particularly preferred embodiment, the cancer is lung cancer, more preferably non-small cell lung cancer (NSCLC) or small cell lung cancer (SCLC), even more preferably NSCLC.

In another particularly preferred embodiment, the cancer is colorectal cancer.

In one preferred embodiment, the proliferative disorder is a leukaemia. Preferably, the leukemia is selected from acute myelogenous leukemia (AML), acute lymphocytic leukemia (ALL), chronic myelogenous leukemia (CML) and chronic lymphocytic leukemia (CLL).

In one highly preferred embodiment, the cytotoxic agent is suberoylanilide hydramic acid (SAHA) and the proliferative disorder is non-Hodgkin's lymphoma or lung cancer.

In another highly preferred embodiment, the cytotoxic agent is sodium butyrate and the proliferative disorder is lung cancer.

In yet another highly preferred embodiment, the cytotoxic agent is irinotecan and the proliferative disorder is colorectal cancer.

In another particularly preferred embodiment, the cytotoxic agent is irinotecan and the proliferative disorder is lung cancer.

In another preferred embodiment, the cytotoxic agent is etoposide and the proliferative disorder is lung cancer or testicular cancer.

In a particularly preferred embodiment, the cytotoxic agent is etoposide and the proliferative disorder is lung cancer.

In one highly preferred embodiment, the combination comprises sapacitabine and SAHA, and the proliferative disorder is selected from NSCLC, AML and CTCL.

In another preferred embodiment, the combination comprises sapacitabine and sodium valproate, and the proliferative disorder is selected from CTCL and AML.

In another preferred embodiment, the combination comprises CNDAC and topotecan, and the proliferative disorder is small cell lung cancer (SCLC).

In one highly preferred embodiment, the combination comprises CNDAC and SAHA, and the proliferative disorder is selected from NSCLC and AML. In one especially preferred embodiment, the proliferative disorder is AML, and for this particular embodiment, CNDAC pre-treatment is even more preferred.

In another preferred embodiment, the combination comprises CNDAC and sodium valproate, and the proliferative disorder is selected from CTCL and AML.

Another aspect of the invention relates to the use of 2'-cyano-2'-deoxy-$N^4$-palmitoyl-1-β-D-arabinofuranosyl-cytosine, or a metabolite thereof, or a pharmaceutically acceptable salt thereof, in the preparation of a medicament for treating cutaneous T-cell lymphoma (CTCL).

Similarly, the invention further relates to a method of treating cutaneous T-cell lymphoma (CTCL) in a subject, said method comprising administering to said subject a therapeutically effective amount of 2'-cyano-2'-deoxy-$N^4$-palmitoyl-1-β-D-arabinofuranosyl-cytosine, or a metabolite thereof, or a pharmaceutically acceptable salt thereof.

In one preferred embodiment of the invention, the 2'-cyano-2'-deoxy-$N^4$-palmitoyl-1-β-D-arabinofuranosyl-cytosine, or a metabolite thereof, or a pharmaceutically acceptable salt thereof is administered in combination with a pharmaceutically acceptable carrier, diluent or excipient.

In one preferred embodiment of the invention, the 2'-cyano-2'-deoxy-$N^4$-palmitoyl-1-β-D-arabinofuranosyl-cytosine, or a metabolite thereof, or a pharmaceutically acceptable salt thereof is administered in combination with one or more other antiproliferative agents.

Pharmaceutical Compositions

In a particularly preferred embodiment, the pharmaceutical product of the invention is in the form of a pharmaceutical composition comprising a pharmaceutically acceptable carrier, diluent or excipient.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients", $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

By way of example, in one preferred embodiment, the prodrug of sodium butyrate is pivaloyloxymethyl butyrate. Preferably, the prodrug of SN-38 is irinotecan.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose. Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In a preferred embodiment, sapacitabine is administered orally.

In another preferred embodiment, irinotecan is administered intravenously.

In yet another preferred embodiment, etoposide is administered orally or intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 2 to 20 mg/kg, more preferably from 0.1 to 1 mg/kg body weight.

By way of guidance, sapacitabine is typically administered in accordance to a physician's direction at dosages between 0.05 to 5 g for an adult human patient. Preferably, the dosage is between 1 and 120 mg/m$^2$ body surface orally. The doses can be given 5 days a week for 4 weeks, or 3 days a week for 4 weeks. Sapacitabine may also be administered at dosages between 1 and 500 mg per dose twice a day. Preferably, these doses may be given in a treatment cycle which comprises administering sapacitabine for 2 to about 6 days per week, for 2 weeks out of 3 weeks. More preferably, the sapacitabine may be given from 3 to 5 days per week for two weeks with 1 week rest. Even more preferably, the sapacitabine may be given for 3, 4 or 5 consecutive days per week for two weeks with 1 week rest. Alternatively, the sapacitabine may be in a treatment cycle which comprises administering sapacitabine for 7 days or 14 days every 21 days, more preferably for 7 consecutive days or 14 consecutive days every 21 days, even more preferably for 7 consecutive days followed by two weeks rest. Dosages and frequency of application are typically adapted to the general medical condition of the patient and to the severity of the adverse effects caused, in particular to those caused to the hematopoietic, hepatic and to the renal system. The total daily dose of sapacitabine can be administered as a single dose or divided into separate dosages preferably administered two, three or four time a day.

By way of guidance, the cytotoxic agent is typically administered in accordance with a physician's direction at dosages between the approved dosages for said cytotoxic agent. Said dosages are available from the Summary of Product Characteristics for each agent which may be obtained from the manufacturer or from the literature e.g. www.emea.eu.int/htms/human/epar/a-zepar.htm.

Preferably, where the cytotoxic agent is etoposide, it is administered by infusion, more preferably, intravenous infusion. Preferably, the etoposide is administered in a dosage of from 100 to 120 mg/m$^2$/day via continuous infusion over 30 to 60 minutes.

Preferably, where the cytotoxic agent is irinotecan, it is administered by infusion into a peripheral or central vein, more preferably by intravenous infusion. Preferably, the irinotecan is administered in a dosage of from 100-400 mg/m$^2$, more preferably from 150-350 mg/m$^2$, even more preferably from 150-200 mg/m$^2$. Preferably, the irinotecan is administered over a 30 to 90 minute period.

Preferably, where the cytotoxic agent is topotecan, it is administered in oral or intravenous forms. For the oral form the recommended dose is 2.3 mg/m$^2$/day once daily for 5 consecutive days repeated every 21 days. For the intravenous form the recommended dose is 1.5 mg/m2 by intravenous infusion over 30 minutes daily for 5 consecutive days, starting on day 1 of a 21-day course.

By way of guidance, the HDAC inhibitor is typically administered in accordance with a physician's direction. Pivanex (pivaloyloxymethyl butyrate) is typically administered at about 2.34 g/m$^2$ per day. Pivanex is preferably administered intravenously. Suberoylanilide hydroxamic acid (SAHA) is typically administered from about 100-600 mg per day. Suberoylanilide hydroxamic acid (SAHA) is preferably administered orally. Valproic acid is typically administered from about 10 to 60 mg/kg when administered orally, or from about 10 to 150 mg/kg when administered intravenously. The total daily dose of HDAC inhibitor can be administered as a single dose or divided into separate dosages preferably administered two, three or four time a day.

Kit of Parts

A further aspect of the invention relates to a kit of parts comprising:
(i) 2'-cyano-2'-deoxy-N$^4$-palmitoyl-1-β-D-arabinofuranosyl-cytosine, or a metabolite thereof, or a pharmaceutically acceptable salt thereof, optionally admixed with a pharmaceutically acceptable diluent, excipient or carrier; and
(ii) a cytotoxic agent selected from: (a) a HDAC inhibitor; and (b) a topoisomerase inhibitor selected from etoposide, topotecan and SN-38, or a prodrug thereof, optionally admixed with a pharmaceutically acceptable diluent, excipient or carrier.

Preferably, sapacitabine, or a metabolite thereof, or a pharmaceutically acceptable salt thereof, and the cytotoxic agent are each in unit dosage form. Preferably, the kit of parts contains a plurality of unit dosage forms of each component, i.e. of components (i) and (ii) above.

Optionally, the kit of parts may further comprise a means for facilitating compliance with a particular dosing regimen, for example, instructions indicating when, how, and how frequently the unit dosage forms of each component should be taken.

The present invention is further described by way of example, and with reference to the following figures, wherein:

FIG. 1 shows that CNDAC and SAHA induce a dose-dependent increase in sub-G1 Hut78 cells.

FIG. 2 shows xenograft data from the combinations of sapacitabine with either irinotectan (CPT-11) or SAHA. In each column, the symbols represent the individual mice and the line represents the average for that group. The error bars represent the standard error of the mean. The data was obtained 22 days after the start of the treatment. This timepoint was immediately after the 21 day treatment regimes have been completed.

EXAMPLES

Material and Methods

Figure 1:
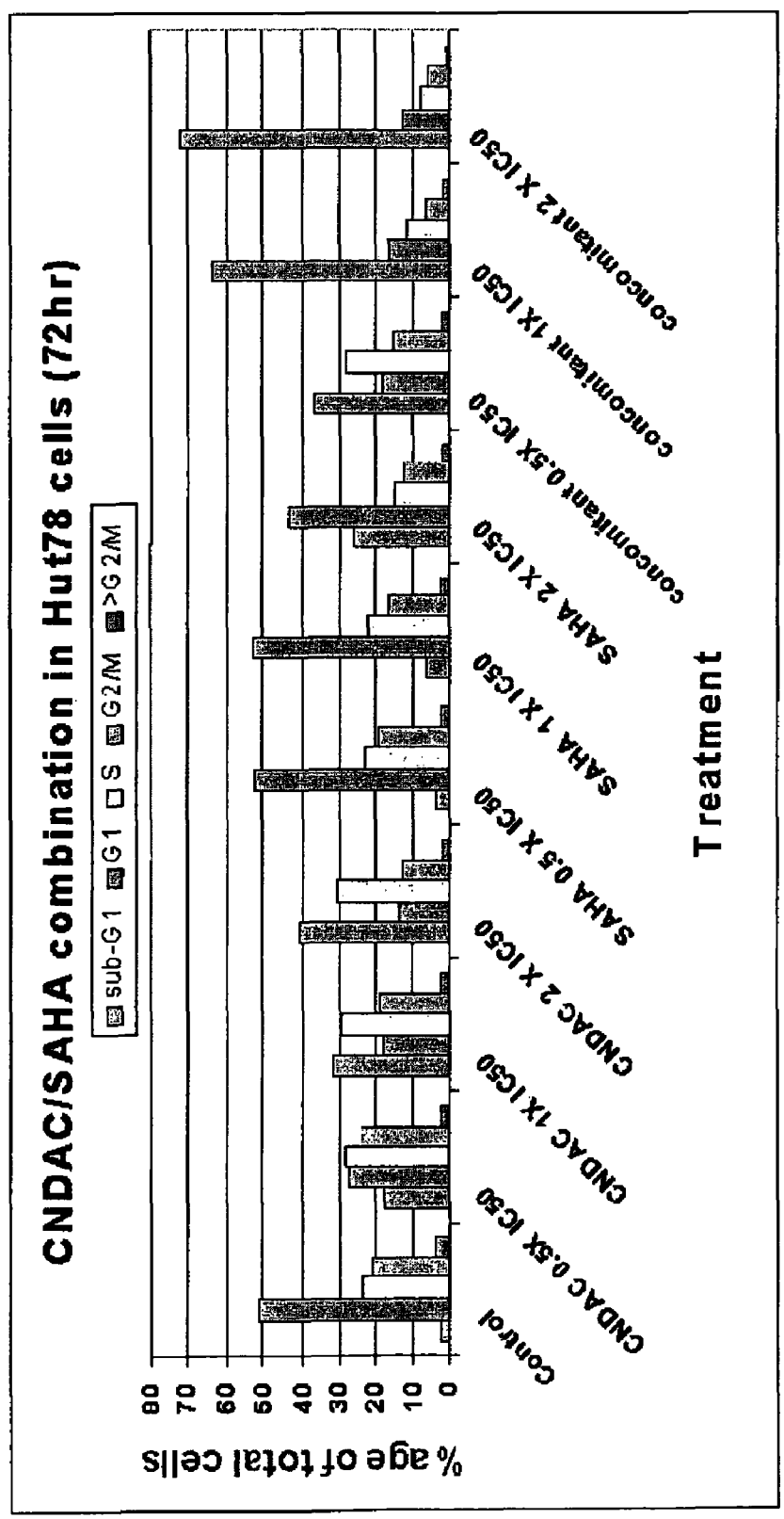

CNDAC was supplied by Cyclacel Ltd. (Dundee, UK). Etoposide was supplied by Sigma. SN-38 was supplied by Abatra technology Co Ltd, Xi'an, China. Irinotectan was supplied by Pfizer. Sodium butyrate, valproic acid and sodium valproate were obtained from Sigma; trichostatin A (TSA) was obtained from AG Scientific, Inc.; SAHA was obtained from Toronto Research Chemicals, Inc. Cell lines H1299, H460, Hut78, MV4-11, HL-60 and PL-21 were obtained from ATCC.

Preparation of Sapacitabine

Sapacitabine was prepared in accordance with the methodology described in Examples 1 and 2 of EP 536936 in the name of Sankyo Company Limited.

Cell Culture

Experiments were carried out in 96-well plates and the cell lines seeded at a density of 2500/well for H1299, 2500/well or 3000/well for H460, 5000/well for HL-60 cells, and 8,000 cells/well for Hut78, MV4-11 and PL-21 cells. In the solid tumour cell lines (H460 and H1299) 24 h treatment and 72 h treatment $IC_{50}$ values were determined for each compound using the Alamar blue assay, whereas only 72 h $IC_{50}$ values were obtained in the suspension cell lines (Hut78, MV4-11, HL60 and PL21). Each compound was then tested in combination with CNDAC using three different treatment regimes: concomitant, CNDAC pre-treatment followed by HDAC inhibitor/topoisomerase inhibitor and CNDAC treatment after pre-treatment with HDAC inhibitor/topoisomerase inhibitor. In Hut78 cells, a concomitant treatment regime was employed, after pre-treatment with CNDAC, SAHA or drug-free medium for 24 h.

Calcusyn Drug Combination Protocol

Slightly different variations of the combination protocol were used in the different cell lines tested, since some cell lines do not adhere to the plates, making aspiration of impracticable.

For the concomitant treatment regime in H460 and H1299 cells, 2-fold serial dilutions of CNDAC, HDAC inhibitor/topoisomerase inhibitor, or both drugs simultaneously were added to cells 24 h after plating, and left for 72 h at 37° C. In the pre-treatment regimes, the first drug was added 2 h after cells were plated, and left for 24 h. Medium was aspirated and replaced with fresh medium containing the second drug, and incubated for 72 h. The two controls for each sequential treatment involved substituting one of the drug treatments with medium. A similar protocol was used in Hut78 cells, although the medium aspiration step was omitted (as the pre-treatment drug could not be removed from these cells, since it is a suspension cell line). AML cell lines (HL60, MV4-11, PL21): Combination analysis was carried out essentially as described for Hut78 cells, except the 72 h drug incubation period was reduced to 48 h in the AML cell lines, to compensate for their fast growth rate.

After drug treatment, the cell number in each well was then estimated by incubating the cells for 1 h in medium containing 10% alamar blue (Roche, Lewes, East Sussex, U.K.) and reading the absorbance at 544-595 nm. Drug interactions were analysed using the commercial software package Calcusyn, which is based on the median effect model of Chou and Talalay (Chou, T. C. & Talalay, P. (1984) Adv. Enzyme Regul. 22, 27-55. Quantitative analysis of dose-effect relationships: the combined effects of multiple drugs or enzyme inhibitors). A Combination Index (C.I.) of 1 indicated an additive drug interaction, whereas a C.I. greater than 1 was antagonistic and a score lower than 1 was synergistic.

Flow Cytometry

Hut78 cells were seeded in 10 cm plates at approximately $5 \times 10^5$ cells/plate and left to settle for 2 h. CNDAC, SAHA or both drugs were added at the indicated concentrations for the times shown (16-72 h treatment). After treatment, cells were harvested and cell cycle analysis was carried our. Cells were pelleted by centrifugation, washed twice in PBS and then fixed overnight in 70% (v/v) ethanol at −20° C. Cells were stained with 50 μg/ml propidium iodide for 20 min and the DNA content analysed on the flow cytometer. Annexin V staining was performed as indicated in manufacturer's instructions, on live, non-fixed cells.

Statistical Analysis and Determination of Synergistic Activity

Effects of drug combinations were evaluated using the Chou and Talalay method which is based on the median-effect principle (Chou T C, Talalay P. Quantitative analysis of dose-effect relationships: the combined effects of multiple drugs or enzyme inhibitors. Adv Enzyme Regul. 1984; 22:27-55). This involves plotting dose-effect curves for each drug and for multiple diluted, fixed-ratio combinations, using the equation: $f_a/f_u=(C/C_m)^m$, where $f_a$ is the cell fraction affected by the drug concentration C (e.g., 0.9 if cell growth is inhibited by 90%), $f_u$ is the unaffected fraction, C is the drug concentration, $IC_{50}$ the concentration required for a half-maximal effect (i.e., 50% inhibition of cell growth), and m is the sigmoidicity coefficient of the concentration-effect curve. On the basis of the slope of the curve for each drug in a combination, it can be determined whether the drugs have mutually nonexclusive effects (e.g., independent or interactive modes of action).

The combination index (CI) is then determined by the equation:

$$CI=[(C)_1/(C_x)_1]+[(C)_2/(C_x)_2]+[\alpha(C)_1(C)_2/(C_x)_1(C_x)_2],$$

where $(Cx)_1$ is the concentration of drug 1 required to produce an x percent effect of that drug alone, and $(C)_1$, the concentration of drug 1 required to produce the same x percent effect in combination with $(C)_2$. If the mode of action of the drugs is mutually exclusive or nonexclusive, then α is 0 or 1, respectively. CI values will be calculated with this equation using different values of $f_a$ (i.e., for different degrees of cell growth inhibition). CI values of <1 indicate synergy, the value of 1 indicates additive effects, and values >1 indicate antagonism. Data were analyzed on an IBM-PC computer using concentration-effect analysis for microcomputer software (Biosoft, Cambridge, UK). For statistical analysis and graphs we will use Instat and Prism software (GraphPad, San Diego, USA). The dose-effect relationships for the drugs tested, alone or in paired combinations, were subjected to median-effect plot analysis to determine their relative potency ($IC_{50}$), shape (m), and conformity (r) in each selected cell line. As stated above, the $IC_{50}$ and m values were respectively used to calculate synergism and antagonism on the basis of the CI equation. Results were expressed as the mean±standard deviation of at least 3 experiments performed in duplicate. In each experiment, cells were exposed to the paired combinations for 48 hours as described above. Means and standard deviations were compared using Student's t-test (two-sided p value).

Western Blotting Analysis

Protein lysates were generated from 10 cm plates that were seeded at approximately $5 \times 10^5$ cells/well, in medium containing 10% FCS. Cells were incubated with CNDAC, SAHA, or both compounds at the indicated concentrations and times prior to harvest. Cells were collected by centrifugation (5 min×2,000 g), washed once with ice-cold buffer A (50 mM HEPES, pH 7.0, 20 mM NaCl, 1 mM DTT, protease inhibitors, 10 mM Sodium pyrophosphate, 10 mM Sodium Fluoride and 1 mM Sodium Orthovanadate), and resuspended in 0.3 ml of the same buffer. Cells were lysed by sonication (2×3 s bursts with probe sonicator), and the protein concentration of each tube determined using the BCA assay. Lysates (20-30 μg protein loaded/well) were resolved on Bis-Tris gels containing 10 or 12% acrylamide and transferred to nitrocellulose for analysis by western blotting. Membranes were blocked for 1 h at room temperature in PBS containing 0.02% (v/v) Tween 20 and 5% (w/v) fat-free dried milk. Antibody incubations were carried out overnight at 2-8° C. in PBS containing 0.02% (v/v) Tween 20 (PBST) containing 3% (w/v) dried milk. Nitrocellulose membranes were probed with the following antibodies:

| Antibody | Source | target protein | dilution used |
|---|---|---|---|
| Cleaved PARP | BD Pharmingen | Cleaved PARP | 1:500 |
| Acetyl-Histone H4 | Upstate | Acetylated Histone H4 | 1:1000 |
| XIAP | Cell Signalling | XIAP | 1:1000 |
| Mcl-1 (S-19) | Santa Cruz | Mcl-1 | 1:1000 |
| Survivin | AbCam | Survivin | 1:500 |
| H2A.X | Upstate | H2A.X | 1:2000 |
| pser139 H2A.X | Upstate | pser139 in H2A.X | 1:2000 |
| pser317 Chk1 | Cell signalling | pser317 in Chk1 | 1:1000 |
| RAD51 | Neomarkers | RAD51 | 1:250 |

Membranes were then washed three times in PBST, and then incubated for 1 h with the appropriate horseradish peroxidase-conjugated secondary antibody (Perbio) at 1:5,000 dilution. Finally, the membranes were washed three times in PBST prior to development using an enhanced chemiluminescence kit (Amersham Corporation, Buckinghamshire, U.K.) or the Millipore Immobilon HRP substrate.

Results

Antiproliferative Effect of CNDAC and SAHA Against a Cutaneous T-Cell Lymphoma Cell Line (Hut78)

Table 1 shows the effect of CNDAC and SAHA against the cutaneous T-cell lymphoma (CTCL) cell line Hut78 cells using three different treatment regimes. The Combination Index values from each drug treatment are shown for ED50, ED75 and ED90 values (the point on the curve where 50%, 75% and 90% of the cells have been killed). Data are the average of three independent experiments.

These results demonstrate that CNDAC and SAHA are highly synergistic in Hut78 cells, with all three treatment regimes tested. Pretreatment with either SAHA or CNDAC appears to slightly enhance the concomitant treatment regime. These data demonstrate that combining CNDAC with SAHA may be a promising treatment regime for treating Cutaneous T-cell Lymphoma (CTCL) cells.

In view of the difficulties in working with a suspended cell line, one drug was tested prior to a combination of the two drugs. This method is equivalent to first testing one drug and then the other drug in a situation where the half-life of the first drug is such that the first drug is still present when the second drug is applied.

CNDAC and SAHA Induce a Dose-Dependent Increase in Sub-G1 Hut 78 Cells

FIG. 1 shows that CNDAC and SAHA induce a dose-dependent increase in sub-G1 Hut 78 cells. Hut78 cells were incubated with 0.5x-2×IC50 CNDAC, 0.5-2×IC50 SAHA, or 0.5-2×IC50 CNDAC+SAHA for 72 h. 1×IC50 values are 0.36 μM for CNDAC and 0.46 μM for SAHA in Hut78 cells. After drug treatment, cells were then harvested, stained with propidium iodide and their DNA content analysed by flow cytometry. SAHA alone had little effect on the cell cycle, except at 2×IC50, where it induced a small increase in sub-G1 cells (those that contain less DNA than normal diploid cells), which are usually dead or undergoing apoptosis. CNDAC treatment induced a dose-dependent increase in sub-G1 cells, which was synergistically enhanced by inclusion of SAHA. These data indicate that CNDAC and SAHA induce a synergistic increase in cells that are dead or dying.

CNDAC and SAHA Induce a Time-Dependent Increase in Sub-G1 Hut78 Cells

Figure 4:
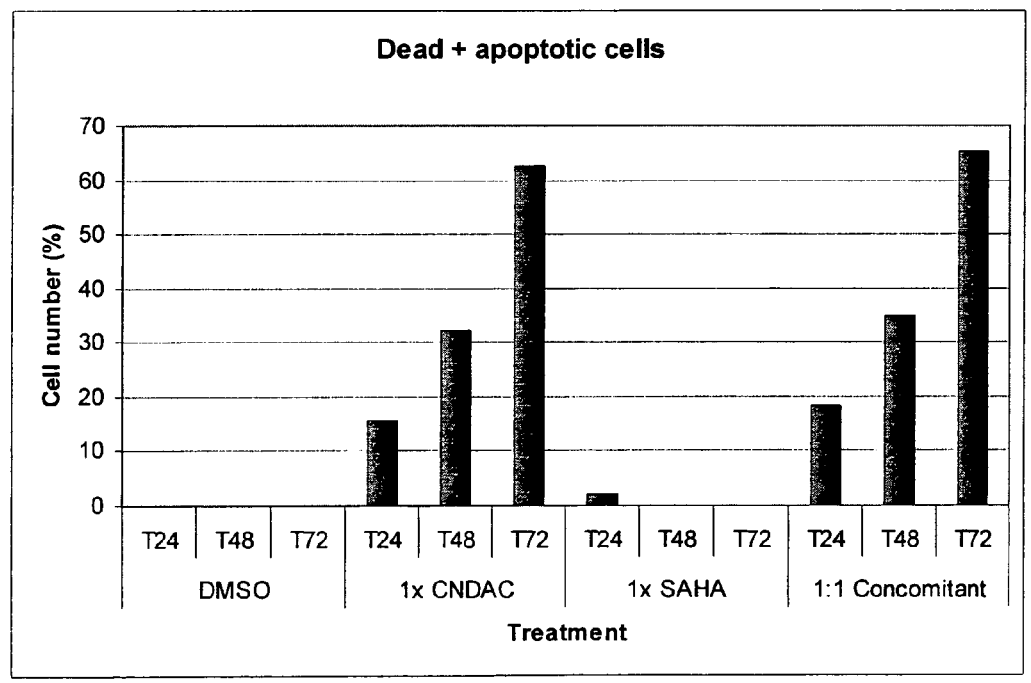
FIG. 4 shows Annexin V staining in dead and apoptotic cells (cell number % vs treatment). The staining indicates that CNDAC and SAHA induce an additive increase in dead/dying Hut78 cells.

FIG. 4 shows that CNDAC and SAHA induce a time-dependent increase in sub-G1 Hut78 cells. Hut78 cells were incubated with 1×IC50 CNDAC, 1×IC50 SAHA, or 1×IC50 CNDAC+SAHA for 16, 24, 48 or 72 h. 1×IC50 values are 0.36 μM for CNDAC and 0.46 μM for SAHA in Hut78 cells. After treatment, cells were then harvested, stained with propidium iodide and their DNA content analysed by flow cytometry. SAHA alone had little effect on the cell cycle and induced a small increase in sub-G1 cells (<2n DNA) which are usually dead or undergoing apoptosis. CNDAC treatment induced a time-dependent increase in sub-G1 cells that became apparent by 48 h treatment and included almost 30% of the cell population by 72 h. CNDAC and SAHA produced a synergistic increase in sub-G1 cells that was apparent by 48 h and involved approximately 70% of the cell population by 72 h. These data indicate that CNDAC and SAHA induce a synergistic increase in cells that are dead or dying and that this effect is significant by 48 h treatment time CNDAC treatment also induced a discrete population of cells in the DNA content that contained 2-3n DNA (S-phase), which could either represent a sub-population of S-phase cells or cells that are dying from G2 phase (4n DNA). If the latter explanation is correct, then CNDAC probably induces a greater proportion of dead/dying cells than is shown in FIG. 4. Overall, these data suggest that the CNDAC/SAHA combination either induces a synergistic or additive increase in cells that are dead or dying.

Antiproliferative Effects of CNDAC and SAHA Against Non-Small Cell Lung Cancer Cells (H460 and H1299)

Table 2 shows the effects of CNDAC and SAHA against H460 and H1299 cells. CNDAC was tested using three different treatment regimes. The Combination Index values from each drug treatment are shown for ED50, ED75 and ED90 values (the point on the curve where 50%, 75% and 90% of the cells have been killed). Data are the average of at least two independent experiments. These results demonstrate that CNDAC and SAHA are synergistic in H1299 cells, with all three treatment regimes tested. These data suggest that combining CNDAC with SAHA may produce a useful treatment regime for treating non-small cell lung cancer (NSCLC) cell lines.

Antiproliferative Effects of CNDAC and Sodium Butyrate Against Non-Small Cell Lung Cancer Cells (H460 and H1299)

Table 3 shows the effects of CNDAC and sodium butyrate against H460 and H1299 cells. These results demonstrate that CNDAC and butyrate generate moderate to strong synergy in H460 and H1299 cells, with all three treatment regimes, showing positive drug interactions. In particular, the results demonstrate that CNDAC pretreatment and concomitant treatment regimes are synergistic in H460 cells. In H1299 cells, butyrate pre-treatment produced a synergistic drug interaction. These data suggest that combining CNDAC with butyrate may produce a useful treatment regime for treating non-small cell lung cancer (NSCLC) cell lines.

Antiproliferative Effects of CNDAC and Topoisomerase Inhibitors Against Non-Small Cell Lung Cancer Cells (H460 and H1299)

Table 4 shows the effects of CNDAC and topoisomerase inhibitors against H460 and H1299 cells. These results demonstrate that combining CNDAC with the topoisomerase inhibitors etoposide, or SN38 (active agent derived from irinotecan) generates synergy in H1299 cells. ED50, 75 and 90 are when 50, 75 and 90% of the cell population has been killed. These data suggest that combining CNDAC with a topoisomerase inhibitor, may produce a useful treatment regime for treating non-small cell lung cancer (NSCLC) cell lines.

CNDAC and HDAC Inhibitors in Combination in Acute Myeloid Leukaemia (AML) Cell Lines CNDAC was tested in combination with the indicated HDAC inhibitors in the AML cell lines HL60, PL21 and MV4-11, using three different treatment regimes (Tables 5 and 6). The Combination Index values from each drug treatment are shown for ED50, ED75 and ED90 values (the point on the curve where 50%, 75% and 90% of the cells have been killed). Data are the average of three independent experiments.

CNDAC and SAHA generated moderate to strong synergy in all three cell lines tested, with little evidence of any antagonism between the compounds. CNDAC pre-treatment was marginally the best treatment regime for this combination.

CNDAC and valproate also produced moderate to strong synergy in all three AML cell lines. With this combination, there was no evidence that any treatment regime was optimal.

These results support the idea of combining CNDAC with HDAC inhibitors in AML cell lines, since most of the combinations generated synergy, with no significant antagonism observed. In addition, valproate and SAHA produced comparable data when combined with CNDAC, arguing that the observed synergy is a result of combining CNDAC with an HDAC inhibitor, and not due to the unique properties of a specific HDAC inhibitor.

CNDAC and SAHA Induce an Additive Increase in Apoptotic/Dead Hut78 Cells

Figure 3:
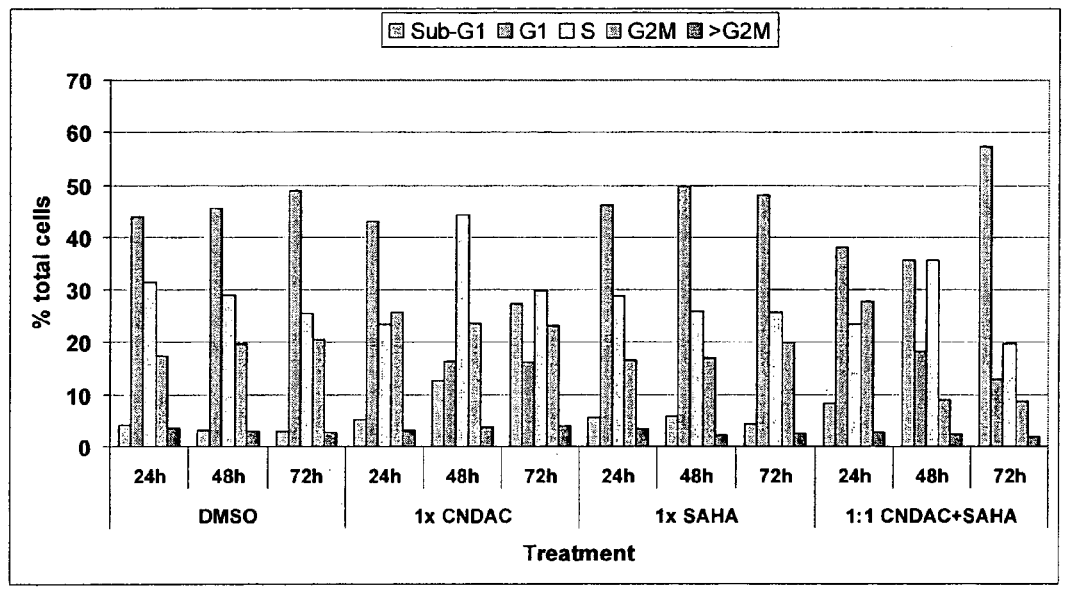
FIG. 3 shows that CNDAC and SAHA induce a synergistic increase in Hut78 cells with a sub-G1 DNA content (% total cells vs treatment).

Hut78 cells were incubated with IC50 CNDAC, SAHA or CNDAC+SAHA for 24 h, 48 h or 72 h. Cells were then harvested, stained with annexin V and analysed on the flow cytometer. Data are representative of two independent experiments. Annexin V labels live cells that are undergoing apoptosis or already dead. SAHA treatment induced a negligible increase in dead/dying cells. FIG. 3 shows that CNDAC single agent treatment and the combination both produced a time-dependent increase in apoptotic/dead cells. Moreover, CNDAC treatment and the combination produced a similar increase in the proportion of apoptotic/dead cells that was comparable in magnitude to the sub-G1 peak observed with the combination (FIG. 3). Taken together, these data suggest that the PI staining in FIG. 3 underestimated the proportion of sub-G1 cells induced by CNDAC treatment, and that the combination only induced an additive increase in apoptotic cells. The synergy detected in the calcusyn analysis (Table 1) is therefore likely to be mainly due to inhibition of cell proliferation.

Analysis of CNDAC and SAHA Combination by Western Blotting in Hut78 Cells

Figure 5:
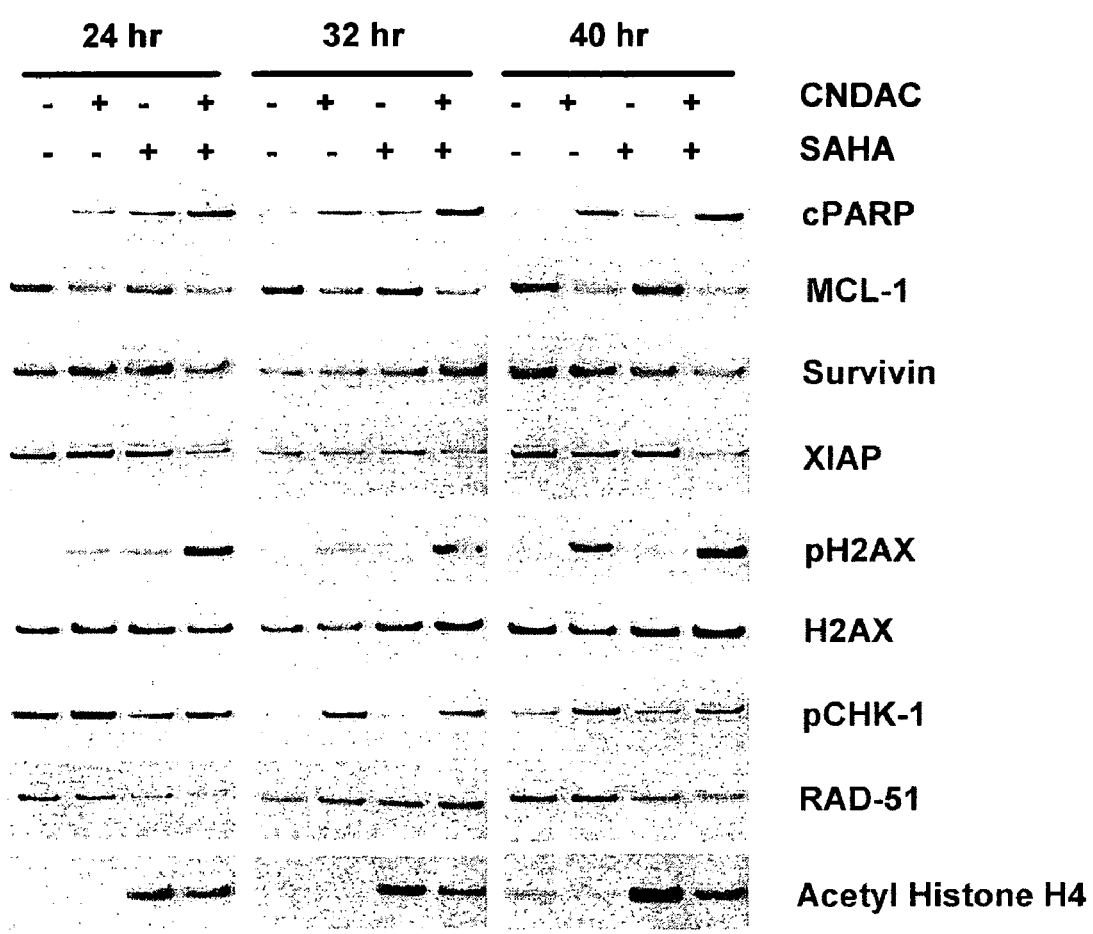
FIG. 5 shows the analysis of CNDAC/SAHA combination by Western Blotting in Hut78 cells. PI and annexin V staining indicate that CNDAC/SAHA combination causes a weak synergistic increase in cell death in Hut78 cells.

Hut78 cells were treated with 1×IC50 CNDAC, SAHA or CNDAC+SAHA for the indicated times. Cells were harvested and the resulting cell lysates analysed by western blotting with the indicated antibodies. Data are representative of two independent experiments (FIG. 5). SAHA treatment induced an increase in Acetyl-histone H4, confirming that the HDAC inhibitor is active in this experiment. The combination induced an additive/synergistic increase in cleaved PARP, which is consistent with the annexin V data presented above (FIG. 4). The increase in apoptosis may be induced by down-regulation of anti-apoptotic proteins, since CNDAC caused a decrease in Mcl-1, and the combination resulted in down-regulation of XIAP and survivin. CNDAC induced an increase in H2A.X phosphorylation at serine 139, which was significantly enhanced by inclusion of SAHA. Phosphorylation of H2A.X at serine 139 is indicative of double strand DNA breaks, and these results suggest that SAHA and CNDAC cause a synergistic increase in this form of DNA damage. Homologous recombination is one of the major repair pathways for double strand DNA breaks, and RAD51 plays a key role in homologous recombination. Therefore, it is possible that the downregulation of RAD51 induced by this combination could play a role in explaining the synergy between these agents, since it would result in decreased repair of double-strand DNA breaks, one of the most deleterious types of DNA damage.

Sapacitabine and SAHA in p388 Xenograft

Figure 6:
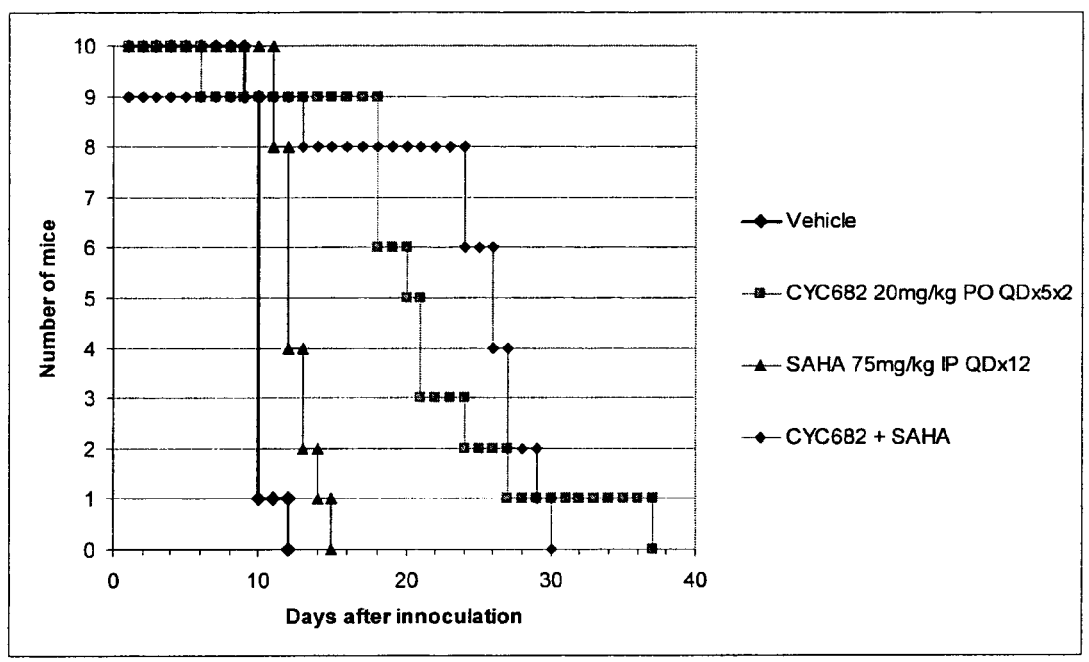
FIG. 6 shows the number of mice vs days after inoculation for various treatment combinations in P388 mouse model (vehicle (control), CYC682 20 mg/kg PO QD×5×2, SAHA 75 mg/kg IP QD×12, or CYC682+SAHA).

The p388 mouse leukaemia xenograft assesses drug combinations by the survival times of the mice in the various treatment arms. In this model, SAHA had very little effect on survival, compared to the vehicle control (see FIG. 6). On the other hand, CYC682 caused a significant increase in the survival time. The CYC682/SAHA combination produced an additive increase in survival, at worst. These data provide evidence that the CYC682/SAHA combination is at least additive in the p388 xenograft model.

In Vivo Studies

Female mice (nu/nu) were obtained from Harlan. Animals were injected subcutaneously with ~1×10$^7$ H358 cells/mouse at a single site on their flanks. Tumours were allowed to grow to ~127 mm³ before being pair-matched by tumour size into treatment groups (10 mice/group). One group was treated with sapacitabine (15 mg/kg) once daily by oral gavage for five consecutive days followed by a two day break; the treatment was then repeated for a total of three cycles. Irinotecan (50 mg/kg) was treated once weekly by intraperitoneal injection for three weeks. SAHA (50 mg/kg) was dosed once daily by oral gavage for 21 consecutive days. All dosing started on day 1 with the irinotecan treatment being given 12 hr prior to the sapacitabine and SAHA treatments; all combination dosing was based on equivalent schedules to the single agent treatments. As a control one group of mice were dosed with the same vehicle/schedule as sapacitabine (2.5% DMA 9.75% Emulphor). Mice were weighed at least twice a week to assess toxicity of the treatments and the tumours were measured with calipers at least twice a week to determine tumour growth. The tumour measurements were converted into volumes using the formula: tumour volume (mm³)= width² (mm)×length (mm)×0.52. The percent tumour growth inhibition was determined with the formula: 1−(Change in treated tumour volume/change in control tumour volume)× 100%. Statistical significance was determined using a two sided unpaired Student's T-test.

Results

Figure 2:
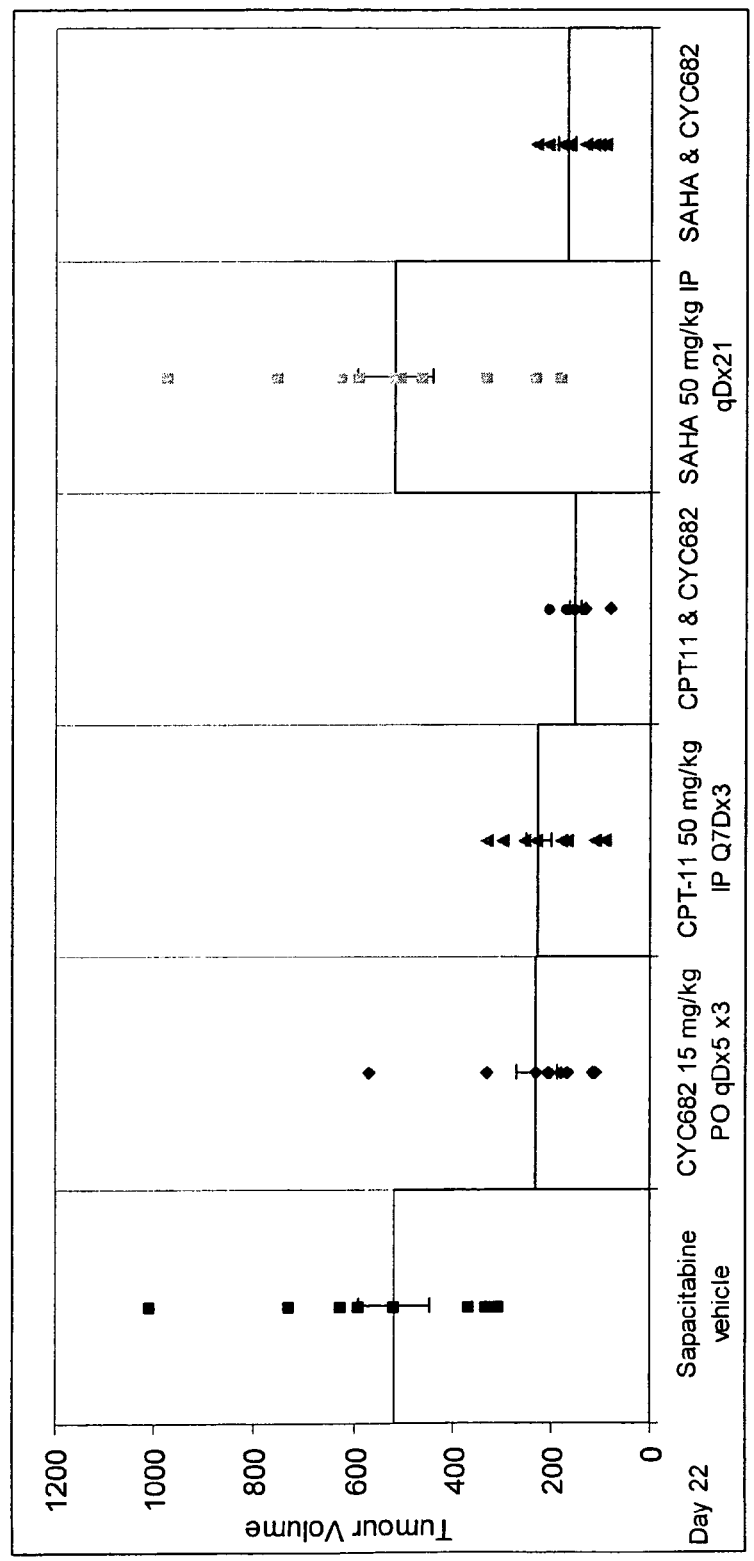

The results from these xenograft experiments are shown in FIG. 2. At day 22 the vehicle control had a mean tumour volume of 517 mm³ while the irinotecan and sapacitabine dosed animals had mean volumes of 225 and 229 mm³ respectively demonstrating that both compounds had activity resulting in ~75% tumour growth inhibition (% TGI). The combination of the two agents had a mean tumour volume of 151 mm³ (94% TGI), demonstrating that the combination is beneficial.

In contrast, SAHA had no effect on tumour growth, having an equivalent mean tumour volume to the control group (517 mm³). The combination of sapacitabine and SAHA had a mean tumour volume of 168 mm³ (89% TGI), since this is smaller than the sapacitabine alone treatment, it suggests that the combination is having a synergistic effect on tumour growth.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1

Analysis of 1-(2-C-cyano-2-deoxy-β-D-arabino-pentafuranosyl)-cytosine (CNDAC) and suberoylanilide hydramic acid (SAHA). Data are the average of three independent experiments.

| Cell Line | | CNDAC/CNDAC + SAHA | SAHA/CNDAC + SAHA | CNDAC + SAHA |
|---|---|---|---|---|
| Hut78 | ED50 | 0.66 | 0.64 | 0.99 |
| (n = 3) | ED75 | 0.56 | 0.47 | 0.7 |
| | ED90 | 0.48 | 0.36 | 0.51 |

TABLE 2

Analysis of CNDAC and SAHA in combination in H460 and H1299 cells. Data are the average of three (H460) or two (H1299) independent experiments.

| Cell Line | | CNDAC Pretreatment | SAHA Pretreatment | Concomitant |
|---|---|---|---|---|
| H460 | ED50 | 0.93 | 1.63 | 0.85 |
| (n = 3) | ED75 | 0.91 | 1.58 | 0.99 |
| | ED90 | 0.94 | 1.57 | 1.18 |
| H1299 | ED50 | 2.24 | 0.66 | 0.63 |
| (n = 2) | ED75 | 0.42 | 0.84 | 0.59 |
| | ED90 | 0.6 | 1.9 | 0.99 |

TABLE 3

Analysis of CNDAC and sodium butyrate in combination in H460 and H1299 cells. Data are the average of three (H460) or two (H1299) independent experiments.

| Cell Line | | CNDAC Pretreatment | Sodium Butyrate Pretreatment | Concomitant |
|---|---|---|---|---|
| H460 | ED50 | 0.8 | 0.99 | 1.00 |
| (n = 3) | ED75 | 0.71 | 0.89 | 0.78 |
| | ED90 | 0.65 | 0.83 | 0.64 |
| H1299 | ED50 | 2.19 | 0.36 | 0.85 |
| (n = 2) | ED75 | 0.61 | 0.48 | 0.93 |
| | ED90 | 1.00 | 1.04 | 1.57 |

TABLE 4

Analysis of CNDAC in combination with a topoisomerase inhibitor in H460 and H1299 cells. Data are the average of three independent experiments.

| Cell Line' | | CNDAC' Pretreatment | Etoposide Pretreatment | Concomitant' |
|---|---|---|---|---|
| H460 | ED50' | 0.51 | 0.65 | 0.53 |
| (n = 3) | ED75' | 0.89 | 0.78 | 0.93 |
| | ED90' | 1.63 | 1.05 | 2.05 |

| Cell Line | | CNDAC Pretreatment | SN38 Pretreatment | Concomitant |
|---|---|---|---|---|
| H1299 | ED50 | 0.58 | 0.53 | 0.45 |
| (n = 3) | ED75 | 1.51 | 0.66 | 1.17 |
| | ED90 | 4.29 | 1.03 | 3.75 |

TABLE 5

Analysis of CNDAC in combination with SAHA in MV4-11, HL-60 and PL-21 cells. Data are the average of two independent experiments.

| Cell Line | Effect | CNDAC pretreatment | SAHA pretreatment | Concomitant |
|---|---|---|---|---|
| MV4-11 | ED50 | 1.19 | 0.87 | 1.04 |
| (n = 3) | ED75 | 0.86 | 0.77 | 0.86 |
| | ED90 | 0.68 | 0.73 | 0.77 |
| HL60 | ED50 | 1.18 | 1.31 | 1.2 |
| (n = 3) | ED75 | 0.76 | 0.97 | 0.97 |
| | ED90 | 0.53 | 0.89 | 0.98 |
| PL21 | ED50 | 0.99 | 1.12 | 1.29 |
| (n = 3) | ED75 | 0.71 | 0.87 | 0.97 |
| | ED90 | 0.53 | 0.7 | 0.73 |

TABLE 6

Analysis of CNDAC in combination with valproate in MV4-11, HL-60 and PL-21 cells. Data are the average of two independent experiments.

| Cell Line | Effect | CNDAC pretreatment | Valproate pretreatment | Concomitant |
|---|---|---|---|---|
| MV4-11 | ED50 | 1.34 | 1.06 | 0.69 |
| (n = 3) | ED75 | 0.86 | 0.79 | 0.64 |
|  | ED90 | 0.61 | 0.64 | 0.64 |
| HL60 | ED50 | 1.93 | 1.43 | 1.16 |
| (n = 3) | ED75 | 1.27 | 1.08 | 0.83 |
|  | ED90 | 0.91 | 0.98 | 0.77 |
| PL21 | ED50 | 1.05 | 1.26 | 1.68 |
| (n = 3) | ED75 | 0.85 | 0.96 | 1.16 |
|  | ED90 | 0.79 | 0.81 | 0.89 |

The invention claimed is:

1. A combination comprising 2'-cyano-2'-deoxy-$N^4$-palmitoyl-1-β-D-arabinofuranosyl-cytosine (sapatacitabine), a metabolite thereof which is 1-(2-C-cyano-2-deoxy-β-D-arabino-pentafuranosyl)-cytosine (CNDAC) or a pharmaceutically acceptable salt of sapatacitabine or CNDAC thereof, and an HDAC inhibitor or a prodrug thereof.

2. The combination of claim 1 wherein the HDAC inhibitor is selected from the group consisting of sodium butyrate, a prodrug thereof, pivaloyloxymethyl butyrate, suberoylanilide hydramic acid (SAHA), sodium valproate, valproic acid, trichostatin A (TSA), PXD101, LAQ824, MS-275, CI-994, SB939, MGCD0103, and depsipeptide.

3. The combination of claim 1, wherein the HDAC inhibitor is suberoyl hydramic acid (SAHA).

4. A pharmaceutical composition comprising the combination of claim 1 and a pharmaceutically acceptable carrier, diluent or excipient.

5. A pharmaceutical product comprising (i) 2'-cyano-2'-deoxy-$N^4$-palmitoyl-1-β-D-arabinofuranosyl-cytosine (sapacitabine), a metabolite thereof which is 1-(2-C-cyano-2-deoxy-β-D-arabino-pentafuranosyl)-cytosine (CNDAC), or a pharmaceutically acceptable salt of sapacitabine or CNDAC, and (ii an HDAC inhibitor or a prodrug thereof.

6. The pharmaceutical product of claim 5, wherein the HDAC inhibitor is selected from the group consisting of sodium butyrate, a prodrug thereof, pivaloyloxymethyl butyrate, suberoylanilide hydramic acid (SAHA), sodium valproate, valproic acid, trichostatin A (TSA), PXD101, LAQ824, MS-275, CI-994, SB939, MGCD0103, and depsipeptide.

7. A pharmaceutical composition comprising the pharmaceutical product of claim 5 and further comprising a pharmaceutical carrier, diluent or excipient.

8. A method of treating a proliferative disorder selected from the group consisting of lymphoma, leukemia and lung cancer, said method comprising simultaneously, separately or sequentially administering to a subject in need thereof (i) 2'-cyano-2'-deoxy-$N^4$-palmitoyl-1-β-D-arabinofuranosyl-cytosine (sapacitabine), a metabolite thereof which is 1-(2-C-cyano-2-deoxy-β-D-arabino-pentafuranosyl)-cytosine (CNDAC), or pharmaceutically acceptable salt of sapacitabine or CNDAC, and (ii) an HDAC inhibitor a prodrug thereof.

9. The method of claim 8 wherein sapacitabine, CNDAC, or pharmaceutically acceptable salt thereof, and the HDAC inhibitor are each administered in a therapeutically effective amount with respect to the individual components.

10. The method of claim 8 wherein the sapacitabine, CNDAC or pharmaceutically acceptable salt thereof, and the HDAC inhibitor are each administered in a sub-therapeutically effective amount with respect to the individual components.

11. The method of claim 8, wherein the lymphoma is cutaneous T-cell lymphoma (CTCL) or non-Hodkin's lymphoma.

12. A kit comprising:
(i) 2'-cyano-2'-deoxy-$N^4$-palmitoyl-1-β-D-arabinofuranosyl-cytosine (sapacitabine), a metabolite thereof which is 1-(2-C-cyano-2-deoxy-β-D-arabino-pentafuranosyl)-cytosine (CNDAC), or pharmaceutically acceptable salt of sapacitabine or CNDAC, optionally admixed with a pharmaceutically acceptable diluent, excipient or carrier; and
(ii) an HDAC inhibitor or a prodrug thereof and wherein the HDAC inhibitor is optionally admixed with a pharmaceutically acceptable diluent, excipient or carrier.

13. The method of according to claim 8 wherein the lung cancer is non-small cell lung cancer (NSCLC).

14. The method according to claim 8, wherein the leukemia is acute myelogenous leukemia (AML).

* * * * *